(12) United States Patent
Totoki

(10) Patent No.: US 7,248,363 B2
(45) Date of Patent: Jul. 24, 2007

(54) PARTICLE SIZE ANALYZER

(75) Inventor: Shinichiro Totoki, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 407 days.

(21) Appl. No.: 10/949,190

(22) Filed: Sep. 27, 2004

(65) Prior Publication Data

US 2005/0083524 A1 Apr. 21, 2005

(30) Foreign Application Priority Data

Oct. 15, 2003 (JP) .............................. 2003-354788

(51) Int. Cl.
*G01N 15/02* (2006.01)
*G01N 21/85* (2006.01)
*G01N 21/25* (2006.01)

(52) U.S. Cl. ...................... 356/336; 356/410; 356/417

(58) Field of Classification Search ............ 250/360.11; 356/72–73, 336–337; 435/4–6
See application file for complete search history.

(56) References Cited

U.S. PATENT DOCUMENTS

| | | | | |
|---|---|---|---|---|
| 4,560,882 A | * | 12/1985 | Nelson et al. | 250/487.1 |
| 4,702,598 A | * | 10/1987 | Bohmer | 356/343 |
| 4,842,406 A | * | 6/1989 | VonBargen | 356/336 |
| 4,922,103 A | * | 5/1990 | Kawajiri et al. | 250/586 |
| 5,420,452 A | * | 5/1995 | Tran et al. | 257/428 |
| 5,552,272 A | * | 9/1996 | Bogart | 435/6 |
| 5,561,515 A | * | 10/1996 | Hairston et al. | 356/28 |
| 6,165,740 A | * | 12/2000 | Fukuda et al. | 435/29 |
| 6,331,438 B1 | * | 12/2001 | Aylott et al. | 436/172 |
| 6,476,395 B2 | * | 11/2002 | Boerner et al. | 250/368 |
| 6,525,325 B1 | * | 2/2003 | Andrews et al. | 250/461.1 |
| 6,648,506 B2 | * | 11/2003 | McGrath et al. | 374/161 |
| 6,813,017 B1 | * | 11/2004 | Hoffman et al. | 356/317 |
| 6,841,778 B1 | * | 1/2005 | Shifflett et al. | 250/339.05 |
| 7,053,380 B2 | * | 5/2006 | Homma et al. | 250/370.11 |

FOREIGN PATENT DOCUMENTS

| | | |
|---|---|---|
| JP | H06-241995 | 9/1994 |
| JP | 2626009 | 4/1997 |
| JP | 2001-033376 | 2/2001 |

* cited by examiner

*Primary Examiner*—Gregory J. Toatley, Jr.
*Assistant Examiner*—Jarreas Underwood
(74) *Attorney, Agent, or Firm*—Manabu Kanesaka

(57) ABSTRACT

A laser diffraction particle size analyzer irradiates a laser beam on particles in a scattered state, and measures a spatial intensity distribution of diffracted and scattered light from the particles. A particle size distribution of the particles is calculated from a result of the measurement. The laser diffraction particle size analyzer includes a laser device for generating an ultraviolet laser beam as a light source for generating a laser beam, and a fluorescent member closely attached to or disposed adjacent to a detecting surface of a photodiode array that measures the spatial intensity distribution of the diffracted and scattered light upon incidence thereof.

4 Claims, 2 Drawing Sheets

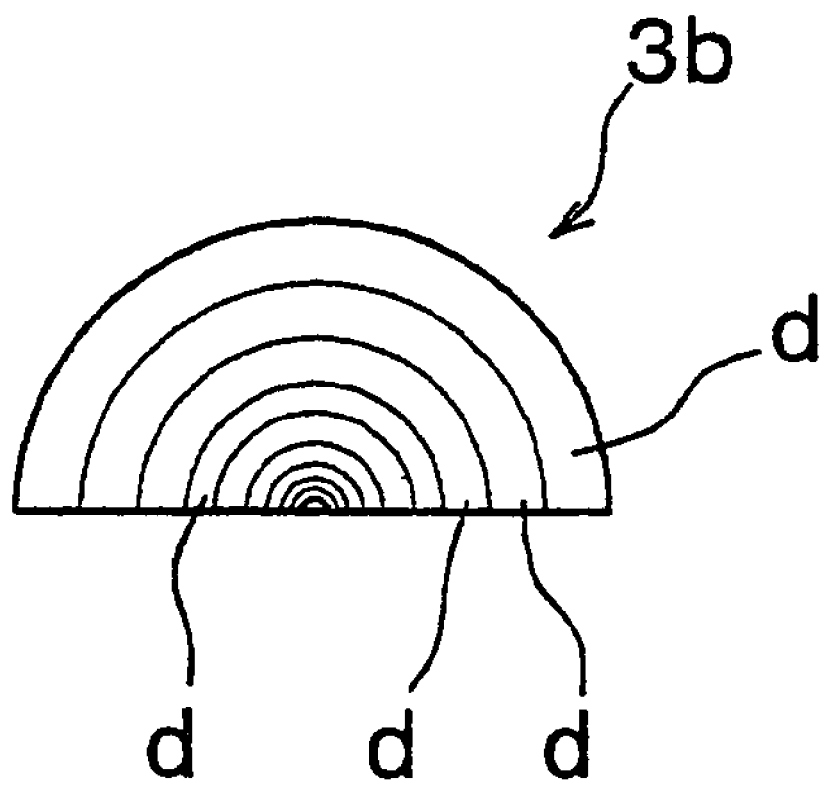

PARTICLE SIZE ANALYZER

BACKGROUND OF THE INVENTION AND RELATED ART STATEMENT

The invention relates to a laser diffraction particle size analyzer, particularly, a particle size analyzer capable of measuring fine particles.

In a general laser diffraction particle size analyzer, a laser beam is irradiated on particles in a scattered state, and a spatial intensity distribution of diffracted and scattered light is measured. The result is converted into a particle size distribution through Mie's scattering theory or Franhofer's diffraction theory (for example, refer to Japanese Patent Publication (Kokai) No. 06-241975). In such a laser diffraction particle size analyzer, a visible laser beam is used for irradiating on particles as the laser beam (for example, refer to Japanese Patent Publication (Kokai) No. 2001-33376). A photodiode array such as a ring detector detects the diffracted and scattered light from the particles (refer to Japanese Patent Publication (Kokai) No. 06-241975).

Incidentally, in such a particle size analyzer, it has been known that a lower limit of particle diameter in measuring a particle size distribution depends on a wavelength of laser beam irradiated on the particles. Accordingly, when the laser beam has a shorter wavelength, it is possible to measure particles with smaller diameters. In the conventional laser diffraction particle size analyzer, the visible laser beam is used, thereby restricting the lower limit of particle diameter in measuring a particle size distribution.

In view of the problem described above, the present invention has been made, and an object of the invention is to provide a particle size analyzer capable of measuring particles with diameters smaller than that the conventional laser diffraction particle size analyzer can measure.

Further objects and advantages of the invention will be apparent from the following description of the invention.

SUMMARY OF THE INVENTION

In order to attain the objects described above, according to a first aspect of the present invention, a laser diffraction particle size analyzer irradiates a laser beam on particles in a scattered state, and measures a spatial intensity distribution of diffracted and scattered light from the particles. A particle size distribution of the particles is calculated from a result of the measurement. The laser diffraction particle size analyzer includes a laser device for generating an ultraviolet laser beam as a light source for generating a laser beam, and a fluorescent member closely attached or disposed adjacent to a detecting surface of a photodiode array that measures the spatial intensity distribution of the diffracted and scattered light for emitting light upon incidence of the diffracted and scattered light.

According to a second aspect of the present invention, the laser device may include a laser device for generating a pulse ultraviolet laser beam.

In the present invention, the laser device for generating the ultraviolet laser beam is provided as the light source for generating the laser beam. Accordingly, it is possible to lower a limit of the measurement range of the particle size. Further, the fluorescent member is disposed adjacent to the detecting surface of the photodiode array that is less sensitive to the ultraviolet light. Accordingly, it is possible to effectively detect the diffracted and scattered light.

That is, the laser device irradiates the ultraviolet laser on the particles as the light source for generating the laser beam, thereby lowering the limit of the measurement range limited by the wavelength of the laser beam. However, the conventional photodiode array and ring detector do not have sufficient sensitivity relative to light in the ultraviolet region diffracted and scattered from the particles, thereby making it difficult to detect. In order to detect the ultraviolet light, a light sensitive tube, a photoelectron multiplier, a Geiger-Mueller counter and the like have generally been used. However, these devices do not have a structure suitable for measuring the spatial intensity distribution of the diffracted and scattered light.

In the present invention, the photodiode array such as a ring detector is used for measuring the spatial intensity distribution of the diffracted and scattered light. Further, the fluorescent member is closely attached to or disposed adjacent to the detecting surface of the photodiode array. The fluorescent member emits light upon receiving the diffracted and scattered light in the ultraviolet region, and the photodiode array detects the light emitted from the fluorescent member. Accordingly, it is possible to measure the particle size distribution of the finer particles, which can not be measured by the conventional measuring device, with a comparatively simple and low cost structure.

In the second aspect of the invention, the pulse laser device is used as the laser light source for irradiating the pulse ultraviolet laser beam. Accordingly, it is possible to reduce cost of the light source. Even if the photodiode is slow to respond to the pulse laser, the fluorescent member is provided on the detecting surface of the photodiode, thereby making it possible to detect.

According to the present invention, the ultraviolet laser beam is irradiated on the particles as the laser beam, and the photodiode array provided with the fluorescent member on the detecting surface thereof detects the diffracted and scattered light from the particles. Accordingly, it is possible to measure the particle size distribution of the finer particles, which can not be measured by the conventional device.

BRIEF DESCRIPTION OF THE DRAWINGS

FIG. 2 is a front view showing an example of a light receiving surface of a ring detector 3b shown in FIG. 1.

DETAILED DESCRIPTION OF PREFERRED EMBODIMENTS

Figure 1:
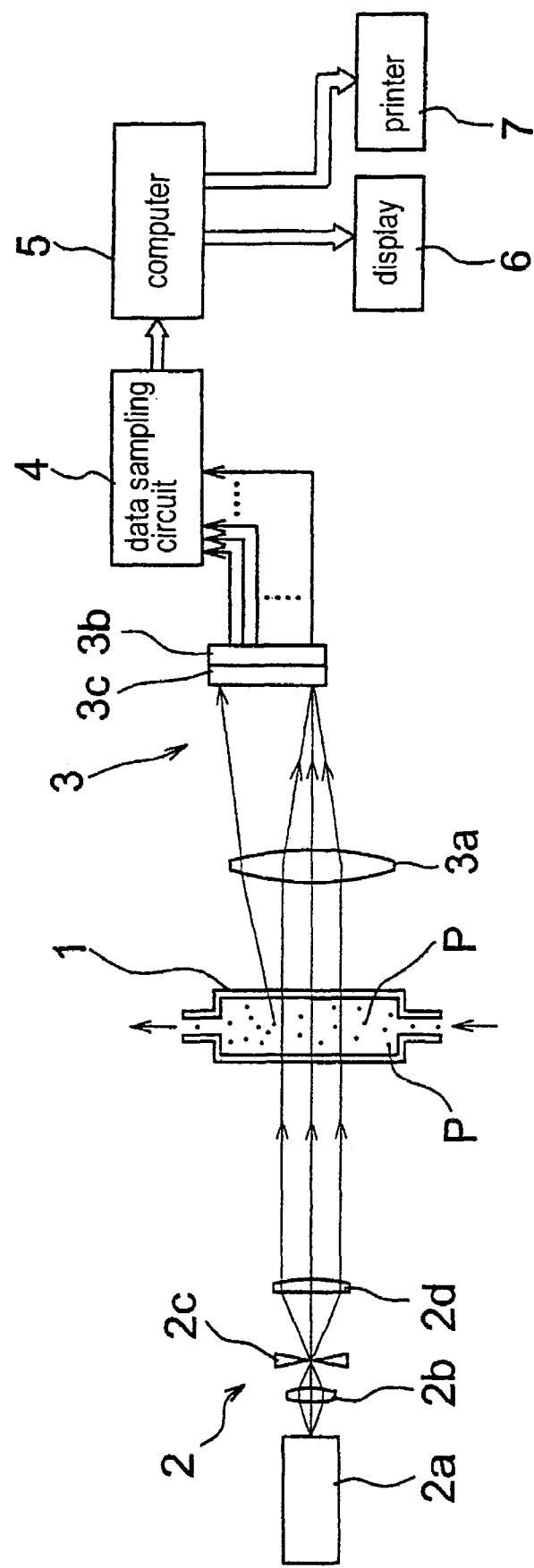
FIG. 1 is a structural diagram showing a laser diffraction particle size analyzer including mechanical and optical structures and electrical structures according to an embodiment of the present invention.

Hereunder, with reference to the accompanying drawings, embodiments of the present invention will be explained in detail. FIG. 1 is a structural diagram showing a laser diffraction particle size analyzer including mechanical and optical structures and electrical structures according to an embodiment of the present invention.

A sample suspension is obtained by dispersing particles to be measured P in a solvent, and flows through a flow cell 1 with a pump and the like as shown by arrows in FIG. 1. The flow cell 1 is formed of, for example, a fused silica and the like capable of transmitting ultraviolet light. An irradiating optical system 2 and a measuring optical system 3 are disposed on both sides of the flow cell 1.

The irradiating optical system 2 is formed of a laser 2a for generating an ultraviolet laser beam, a condenser 2b, a spatial filter 2c and a collimator lens 2d. The laser 2a for generating the ultraviolet laser beam may include a laser device formed of a semiconductor exciting solid laser and a nonlinear optical crystal for generating an ultraviolet laser beam having a wavelength of 266 nm, or a He—Cd gas laser for generating an ultraviolet laser beam having a wavelength of 325 nm.

The measuring optical system 3 is formed of a condenser 3a, a ring detector 3b, and a fluorescent member 3c attached on or disposed adjacent to a detecting surface (light incident surface) of the ring detector 3b. As shown in FIG. 2, the ring detector 3b is a photodiode array formed of photodiodes with different radii disposed concentrically and having independent reception surfaces d (detecting surfaces) formed in a full ring, a half ring or a quarter ring shape. The fluorescent member 3c may include, for example, ZnS for generating fluorescent light upon incidence of the ultraviolet light. A paint of the fluorescent member 3c may be coated on the detecting surfaces d of the ring detectors 3b. Alternatively, the fluorescent member 3c may be dispersed in a transparent glass and attached to the surface of the ring detectors 3b. The ring detector 3b and the fluorescent member 3c are disposed such that the surface of the fluorescent member 3c is positioned at a focal point of the condenser 3a.

The photodiodes of the ring detector 3b send output to a data sampling circuit 4. The data sampling circuit 4 is essentially formed of an amplifier for amplifying the outputs from the photodiodes of the ring detector 3b separately, and an A-D converter for digitalizing outputs from the amplifier. The digitalized outputs of the photodiodes are sent to a computer 5 as spatial intensity distribution data of the diffracted and scattered light from the particles P (described later). The computer 5 converts the spatial intensity distribution data of the diffracted and scattered light into a particle size distribution of the particles P through known algorithm based on Mie's scattering theory or Franhofer's diffraction theory. A result is displayed on a display device 6 or printed out from a printer 7.

In the embodiment described above, when the ultraviolet laser beam is irradiated on the particles P dispersed in the flow cell 1, the laser beam is diffracted and scattered by the particles P. The diffracted and scattered light is condensed by the condenser 3a, and a diffracted and scattered image is formed on a surface of the fluorescent member 3c. When the image is formed, the fluorescent member 3c emits light corresponding to a quantity of light according to an incident position thereof. The ring detector 3b receives light on the detecting surface thereof. Accordingly, the photodiodes of the ring detector 3b output signals corresponding to the quantity according to the diffracted and scattered angle, i.e. a spatial intensity distribution of light diffracted and scattered by the particles P.

As described above, the lower limit of the measurement range of the particle size distribution depends on the wavelength of the laser beam irradiated on the particles P. In the embodiment, the ultraviolet laser beam is used. Accordingly, it is possible to measure the particle size distribution of the particles having a diameter range smaller than that the conventional device can measure. Further, the fluorescent member 3c is attached or bonded to the detecting surfaces d of the ring detector 3b, and any special optical system is not used except the laser 2a, thereby obtaining the advantages described above at low cost.

When a pulse laser device generating a pulse ultraviolet laser beam is used as the laser 2a, it is possible to further reduce cost. In this case, the fluorescent member 3c may be formed of a material having an excellent light-accumulating property or after-glowing property, so that even if the laser beam is a short pulse, the photodiodes of the ring detector 3b can respond, thereby effectively detecting the fluorescence.

In the embodiment, the condenser and the ring detector with the fluorescent member are provided for detecting the diffracted and scattered light with a specific forward angle. Alternatively, the photodiodes may be arranged for detecting the scattered light with a specific side or rear angle, and the fluorescent member may be disposed on the detecting surfaces of the photodiodes.

The disclosure of Japanese Patent Application No. 2003-354788 filed on Oct. 15, 2003 is incorporated in the application.

While the invention has been explained with reference to the specific embodiments of the invention, the explanation is illustrative and the invention is limited only by the appended claims.

What is claimed is:

1. A particle size analyzer for determining a particle size distribution of particles, comprising:
   a light source for irradiating an ultraviolet laser beam on the particles,
   a fluorescent member for emitting fluorescent light when the fluorescent member receives light diffracted and scattered from the particles, and
   a photodiode array having a detecting surface disposed adjacent to the fluorescent member for receiving the fluorescent light from the fluorescent member to obtain a spatial intensity distribution of the light diffracted and scattered from the particles,
   wherein said fluorescent member is a paint coated on the detection surface of the photodiode array.

2. A particle size analyzer as claimed in claim 1, wherein said light source generates a pulse laser beam.

3. A particle size analyzer as claimed in claim 2, further comprising a flow cell for a allowing the particles to flow therein, said flow cell being disposed between the light source and the fluorescent member and made of a material to permit the ultraviolet laser beam to pass therethrough.

4. A particle size analyzer as claimed in claim 1, wherein said fluorescent member contains ZnS for generating fluorescent light upon incidence of the ultraviolet laser beam.

* * * * *